(12) United States Patent
Glynn

(10) Patent No.: US 10,117,570 B2
(45) Date of Patent: Nov. 6, 2018

(54) NON-INVASIVE SPECTROPHOTOMETER AND RELATED METHOD

(75) Inventor: Christopher Glynn, Standlake (GB)

(73) Assignee: MURWILLUMBAH MANUFACTURING LIMITED, Oxon (GB)

( * ) Notice: Subject to any disclaimer, the term of this patent is extended or adjusted under 35 U.S.C. 154(b) by 133 days.

(21) Appl. No.: 13/574,137

(22) PCT Filed: Jan. 19, 2011

(86) PCT No.: PCT/GB2011/050087
§ 371 (c)(1),
(2), (4) Date: Aug. 20, 2012

(87) PCT Pub. No.: WO2011/089427
PCT Pub. Date: Jul. 28, 2011

(65) Prior Publication Data
US 2012/0307209 A1 Dec. 6, 2012

(30) Foreign Application Priority Data
Jan. 21, 2010 (GB) .................................. 1000973.6

(51) Int. Cl.
*A61B 3/10* (2006.01)
*A61B 3/11* (2006.01)
*A61B 5/1455* (2006.01)

(52) U.S. Cl.
CPC .................... *A61B 3/10* (2013.01); *A61B 3/11* (2013.01); *A61B 5/14555* (2013.01)

(58) Field of Classification Search
CPC ......... A61B 3/113; A61B 3/1233; A61B 3/12; A61B 3/10; A61B 3/1015; A61B 3/102; A61B 5/14532; A61B 3/0008; A61B 3/0025; A61B 2019/465; A61B 2017/00057; A61B 2017/00061;
(Continued)

(56) References Cited

U.S. PATENT DOCUMENTS 5,949,535 A  9/1999  Hall
6,381,015 B1  4/2002  Sonehara
(Continued)

FOREIGN PATENT DOCUMENTS

GB  2422660 A  8/2006
WO  WO09122114 A1  10/2009

*Primary Examiner* — Ricky Mack
*Assistant Examiner* — Daniele Manikeu
(74) *Attorney, Agent, or Firm* — Kilpatrick Townsend and Stockton LLP

(57) ABSTRACT

The present invention provides for a device for use in non-invasive inspection measurement and/or monitoring of a human or animal subject's eye, the device having a first optical system which comprises illumination means for selectively directing illumination light onto a selected structure of the eye for direct and diffuse reflectance there from and for providing the illumination light in one or more pulses, receiving means for receiving light returning from the eye as a result of illumination by the illumination light and arranged to record the returning light intermittently at a selected timing relative to the pulse(s) of illumination light so as to discriminate between directly or diffusely reflected light returning from the selected structure and other reflected light for analysis of the said directly or diffusely reflected light.

15 Claims, 7 Drawing Sheets

(58) Field of Classification Search
CPC .. A61B 2017/00172; A61B 2018/2261; A61B 5/0059; A61B 5/0261; A61B 2018/00666; A61B 3/117; G06F 3/013
USPC ........ 351/210, 211, 221, 246, 204, 206, 209
See application file for complete search history.

(56) References Cited

U.S. PATENT DOCUMENTS

| | | | |
|---|---|---|---|
| 2005/0007551 A1* | 1/2005 | Wakil | A61B 3/107 351/205 |
| 2007/0232874 A1* | 10/2007 | Ince | A61B 5/0261 600/320 |
| 2008/0044063 A1 | 2/2008 | Friedman | |
| 2008/0278688 A1* | 11/2008 | Glynn | 351/221 |
| 2009/0263115 A1* | 10/2009 | Suzuki | A61B 3/14 396/18 |
| 2010/0056928 A1* | 3/2010 | Zuzak | A61B 5/0071 600/476 |
| 2010/0160809 A1* | 6/2010 | Laurence | A61B 5/01 600/549 |
| 2010/0245764 A1* | 9/2010 | Munger | A61B 5/0066 351/206 |
| 2011/0001930 A1* | 1/2011 | Levecq | A61B 3/1015 351/209 |
| 2011/0096292 A1* | 4/2011 | Saito | G02B 26/06 351/206 |

\* cited by examiner

NON-INVASIVE SPECTROPHOTOMETER AND RELATED METHOD

The present invention relates to a non-invasive spectrophotometer, and related method in particular for use in the non-invasive inspection, measurement and/or monitoring of physical and physiological features of a human or animal subject's eye and/or bodily functions in vivo. The device and method relate, for example, to such inspection, measurement and monitoring that uses one or more light beams directed at, and returning from various parts of the subject's eye(s) to provide analysable data.

The measurement and/or monitoring of the features and functions of a human or animal body can prove necessary in many different situations. Previously blood samples have been taken from the patient or animal and constituents have been measured by spectrophotometry. It is also known to measure the constituents in the blood of the patient or of the animal by bringing a spectrophotometer into contact with the patient or the animal, for example by using modified contact lens systems. The eye, which is the only part of the body that is designed to transmit light, can therefore act as both a cuvette or an integrated sphere of a spectrophotometer differentiated by time.

WP90/12534 describes apparatus for monitoring body functions by directing light into the eye and analysing the light returning there from. It also describes a pupillometer for measuring the size of the pupil. WO02/071932 describes an improvement to such apparatus in which an alignment means determines the position of the centre of the pupil using a pupillometer to assist in aligning the optical system directing light into the eye. This disclosure of both these specifications is hereby incorporated in the current specification.

The present invention seeks to provide for a device and related method for inspecting, measuring and or monitoring a human or animal body, and in particular the eye thereof, and having advantages over known such devices and methods.

According to one aspect of the present invention there is provided a device for use non-invasive inspection, measurement and/or monitoring of a human or animal subject's eye, the device having a first optical system comprising illumination means for selectively directing illumination light onto the selected structure of the eye for direct reflectance or otherwise therefrom and for providing the illumination light in one or more pulses, receiving means arranged for receiving light returning from the eye as a result of the illumination by the illumination light and arranged to record the returning light intermittently at a selected timing relative to the pulse(s) of illumination light so as to discriminate between directly reflective light returning from the selected structure and diffusely reflective light, for analysis of the said both directly and diffusely reflected returning light.

The invention proves particularly advantageous insofar as it can be arranged to employ particular features of the eye as part of a spectrophotometer for the inspection and/or analysis or measurement and monitoring of an anatomical and physiological characteristics of the eye.

As discussed further below, the subject's eye, and various structural characteristics thereof, can function as a cuvette when monitoring/analysis of the subject's eye by direct reflectance from selected structures within the posterior chamber of the eye is required while the invention advantageously has the option of inspection and monitoring of diffuse reflectance from within the posterior chamber of the eye when functioning as an integrated sphere.

According to another aspect of the present invention there is provided a method of non-invasive inspection, measurement and/or monitoring of a human or animal subject's eye in which one or more pulses of illumination light are directed selectively onto a structure of the eye for direct reflectance or otherwise therefrom and wherein the light returning from the eye as a result of such an illumination is recorded intermittently at a timing relative to said one or more pulses so as to discriminate between directly reflected light returning from the selected structure and other reflective light for analysis of the said directly reflected returning light.

According to yet another aspect of the present invention there is provided a method of non-invasive inspection, measurement and/or monitoring of a human or animal subject's eye in which one or more pulses of illumination light are directed selectively onto a structure in the anterior chamber of the eye for direct and/or diffuse reflectance or otherwise therefrom and wherein the light returning from the anterior chamber of the eye as a result of such an illumination is recorded intermittently at a timing relative to said one or more pulses so as to discriminate between directly and/or the diffusely reflected light returning from the selected structure and other reflective light for analysis of the said directly and/or the diffusely reflected returning light.

The device can therefore be arranged to provide one or more pulses of illumination light to illuminate features of the eye, and to record the returning light pulse of the illumination, such that direct and/or diffuse reflections from different parts of the eye, or the interior thereof can be specifically identified or discriminated against. The recording period may commence immediately at the end of the illumination pulse, or at a predetermined time period thereafter or may overlap with the end of the illumination pulse.

In addition to discriminating between the required reflected light and other reflected light by way of the controlled relationship between the illuminating and the received light pulses, the optical characteristics of structures within the eye can further be advantageously employed within the present invention.

For example, water within the vitreous humor acts to absorb wavelengths generally above 1400 nm and so this can advantageously be employed as a natural filter when considering the reflected light. The distance that the light travels between the lens and the retina at the back of the adult eye being approximately 48 mm of vitreous humor is an important aspect of this filter For example, when receiving and analyzing the reflected light, any light received above 1400 nm can therefore only have arisen through direct or diffuse reflectance from other structures and not from the area of interest. Likewise, when considering any reflectance arising through use of the eye as an integrating sphere, i.e. when considering diffuse reflectance, light of wavelengths above 1400 nm can be ignored and as such would not form a component part of the diffuse reflectance from the retina.

The device and method of the present invention of the eye as an integrated sphere can therefore advantageously employ light of an appropriate selected wavelength having regard to the natural filtering capability of the liquid within the vitreous humor.

The majority of the returning light can then be determined to be either light returning from the retina, preferably diffuse light which has undergone multiple reflections within the eye before exiting through the pupil, or light directly and or diffusely reflected from one or more specific features of the eye. Thus, if required, the arrangement is preferably such that the illumination light reflected directly or diffusely by other parts of the eye is not processed, or alternatively it is only light reflected by specific features of the eye that is processed. The eye is then advantageously used as a cuvette and/or an integrating sphere and can serve to ensure that illumination of the eye is not affected by spatial, angular or polarisation changes in the illumination light. As will be described further below, this provides further significant advantages over known devices in which illumination and recording is carried out simultaneously and in which direct reflectance is discriminated against.

As will be appreciated, an optical system employing the present invention may be provided by modifying a standard spectrophotometer to record pulsed or intermittent light signals. The general principles of using such spectrophotometric techniques are described in WO90/12534 as referred to above.

In the spectroscopy filed, the eye is in effect the cuvette and/or the integrated sphere of the body, since it is the only part of the body that is designed to transmit light. Thus, measurement of the characteristics of light reflected from the eye can give an indication of physical and physiological characteristics of the eye and also of characteristics of bodily functions in general. In addition, the present invention enables the ability of the eye to act as both a cuvette and an integrating sphere at the same time.

In a preferred arrangement, the device can comprise a second optical system for measuring the pupil size, e.g. by modifying a standard pupillometer, such as that described in U.S. Pat. No. 5,784,145. Further, the general principles of using pupillometry in this context are described in the applicant's previous International Patent Applications Nos. WO90/12534 and WO02/071932.

Preferably, the device is also provided with alignment means, such as that described in WO02/071932, controllable either directly by, or independently of the subject, for example by use of manually operated lever(s), button(s) joystick(s) and/or one or more computer mice. The alignment means provides a variable focus capability to the system and may optionally operate in an automatic way without personal intervention from either the subject or the clinician. Indeed, activation of such alignment may also be automatically initiated by the first optical system, once the location of the pupil has been determined. This is a particularly advantageous arrangement for achieving the required "focussing" of the present invention so as to direct the output light to that part of the eye requiring inspection or monitoring.

In one embodiment, the second optical system is adapted to determine the location of the edge(s) of the pupil(s), so as to allow calculation of the centre of the pupil(s). The second optical system may also be used to provide iris recognition to determine and record the identity of the subject.

Of course, while for some aspects of the invention it might be preferred that the illumination light be focussed in the plane of the pupil, in some embodiments, this need not be done and the light simply can be directed towards the eye on as to enter through the pupil and illuminate the retina. In this manner the amount of light illuminating the area of interest is controlled. Alternatively, or in addition, there is the requirement to focus the light on a particular structural feature of the eye, such as the cornea, aqueous humor, lens, iris, vitreous humor and/or retina.

In one arrangement, the first and second light systems can comprise one or more optical fibre(s) for transmitting light towards the eye(s). In a particularly preferred arrangement, the optical fibre(s) can be arranged to function as both the light input means and the light receiving means.

Of course, the first light system may be arranged to monitor the intensity of light of a selected wavelength returning from the retina of the eye.

Alternatively, the first light system may be arranged to monitor the intensity of light of different wavelengths returning from one or more structures of the eye, thereby enabling an absorbance/reflectance characteristic of the structure e.g. the retina to be determined.

The first and second optical systems may have parts in common. Thus, for example, the first and second receiving means may be provided by the same unit. Likewise, if desired, the first and second light systems may use the same processing means.

Of course, it will be appreciated that the device of the present invention employs advantageously adaptable and accurate focusing means for directing the illumination light onto the desired structure forming part of the human or animal subject's eye so as to allow for the ready and accurate monitoring, measurement and/or analysis of the inherent characteristics of such structural element.

According to a further aspect of the invention, there is provided the use of a subject's eye as a cuvette and/or integrated sphere in the optical inspection, measurement and/or monitoring of one or more structures of the eye for the non-invasive inspection, measurement and/or monitoring of physiological and/or physical changes in structures within the eye.

Other preferred or optional features of the invention will be apparent from the following description and from the subsidiary claims of the specification.

It should be appreciated that the expression "human or animal subject's bodily function" used herein is intended to include the wide variety of different functions that a medical or veterinary practitioner may wish to non-invasively inspect, monitor or measure. In particular, it is intended to include the measurement and/or monitoring of any substances and changes in the blood of the retina and any biochemical (organic or inorganic) changes in the cells of the retina of the subject. In addition, any or all of these changes can be measured and/or monitored in conjunction with changes in the electrical, biochemical or pathological activity of the retina or of the brain, and in addition to changes in the physical and/or physiological changes within the eye.

Also, the term "light" as used herein is, unless otherwise specified, intended to include visible wavelengths and non-visible wavelengths such as infra-red, near infra-red and ultra-violet light, that are non-injurious to the eye and the structures contained within the eye. An advantage of using non-visible wavelengths in the cuvette for direct reflectance is that the pupil size does not change when the eye receives such wavelengths. For diffuse reflectance the converse is an advantage, visible light will cause constriction of the pupil and so enhance the efficiency of the eye as an integrated sphere.

The present invention will now be described in further detail by way of the following non-limiting examples with reference to the drawings, in which.

Figure 1:
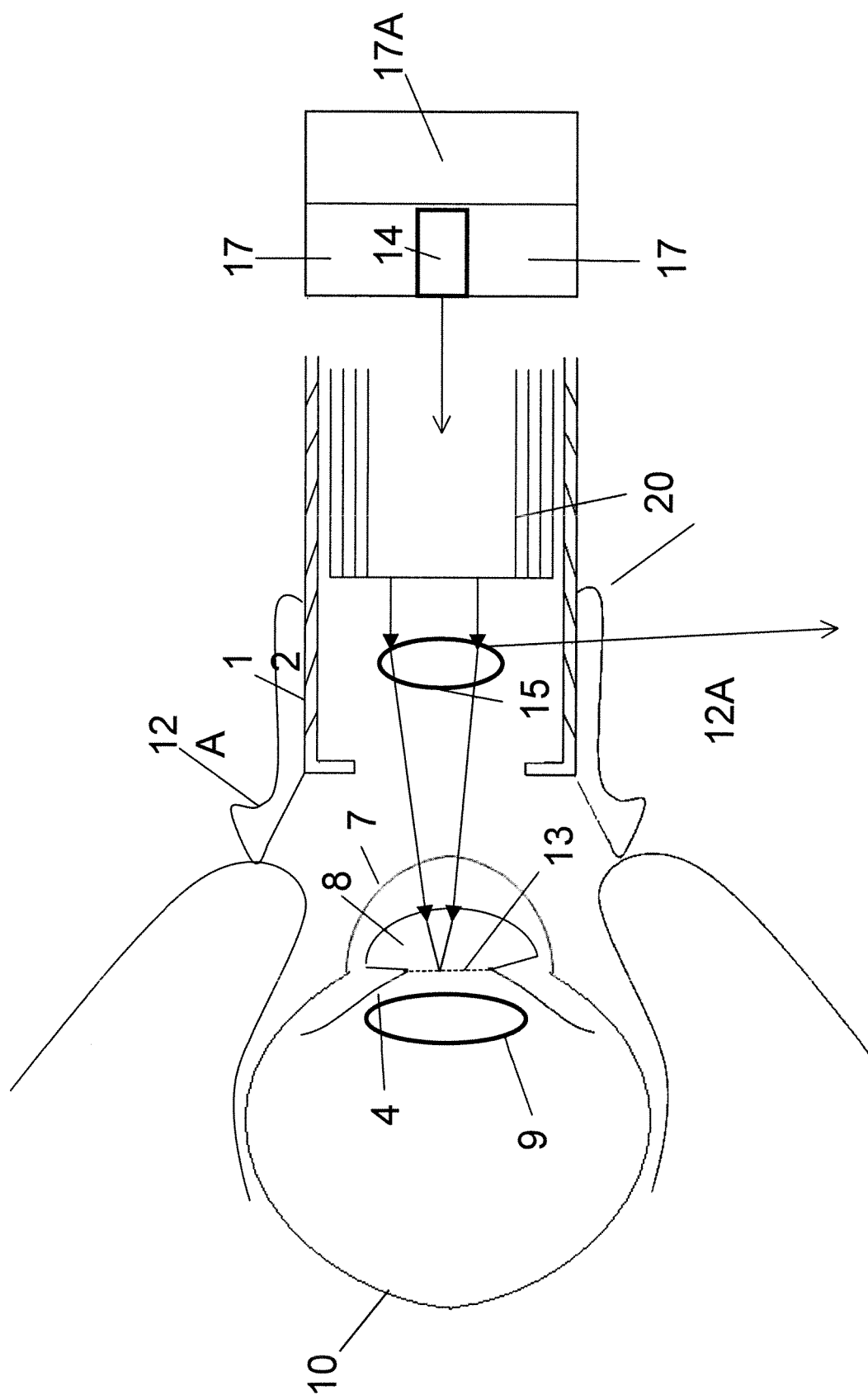
FIG. 1 shows a schematic representation of the first optical system of an embodiment of the present invention during illumination of a structural feature of an eye.
Figure 2:
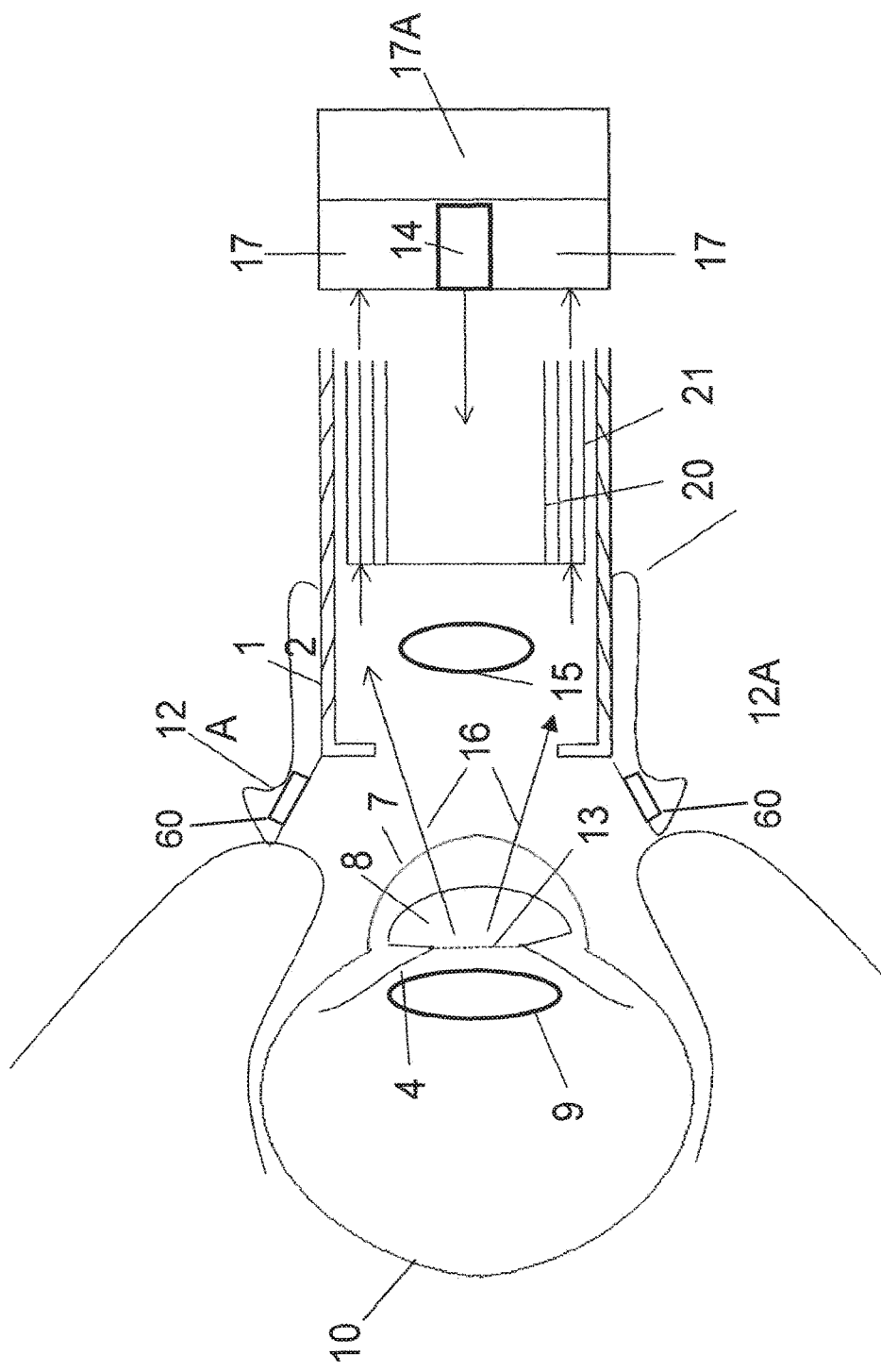
FIG. 2 shows a schematic representation of the first optical system of FIG. 1 during receipt of light returning from the anterior chamber of the eye although noted that light needs to be reflected from the posterior chamber as well.

In FIG. 1, a first optical system is shown that comprises a first light source 14 directing light to focussing means 15 mounted in a housing 12 for focussing light preferably in a controllable and selective manner to any required structural feature and/or region of the eye. In this illustrated embodiment the selected feature is the lens 9 of the eye, although in the illustration of FIG. 3, the feature is the iris 4 or more specifically the plane of the pupil 13 (so illumination is independent of pupil size) and so as to direct the light onto the retina 10 of the eye. In FIG. 2, first receiving means 17 receives directly reflected light 16 returning from the lens 9 or other structures in the anterior chamber of the eye. A second receiving means 60 for diffuse reflected light from the structures of the anterior chamber situated at an angle of 45° on the cowl 12 as shown schematically in FIG. 2.

Figure 3:
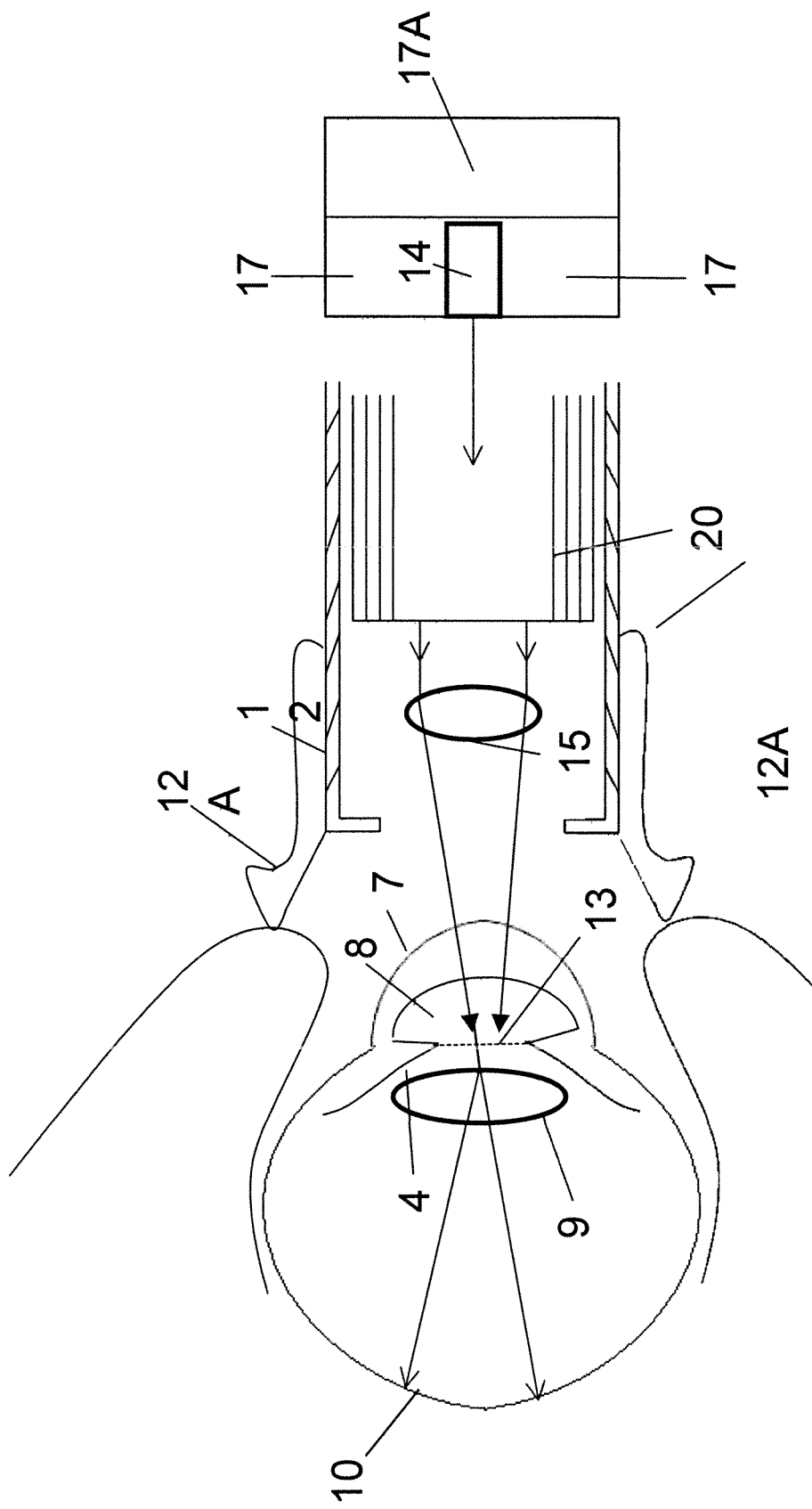
FIG. 3 shows a schematic representation of the first optical system of an embodiment of the present invention during illumination of the posterior chamber of an eye.
Figure 4:
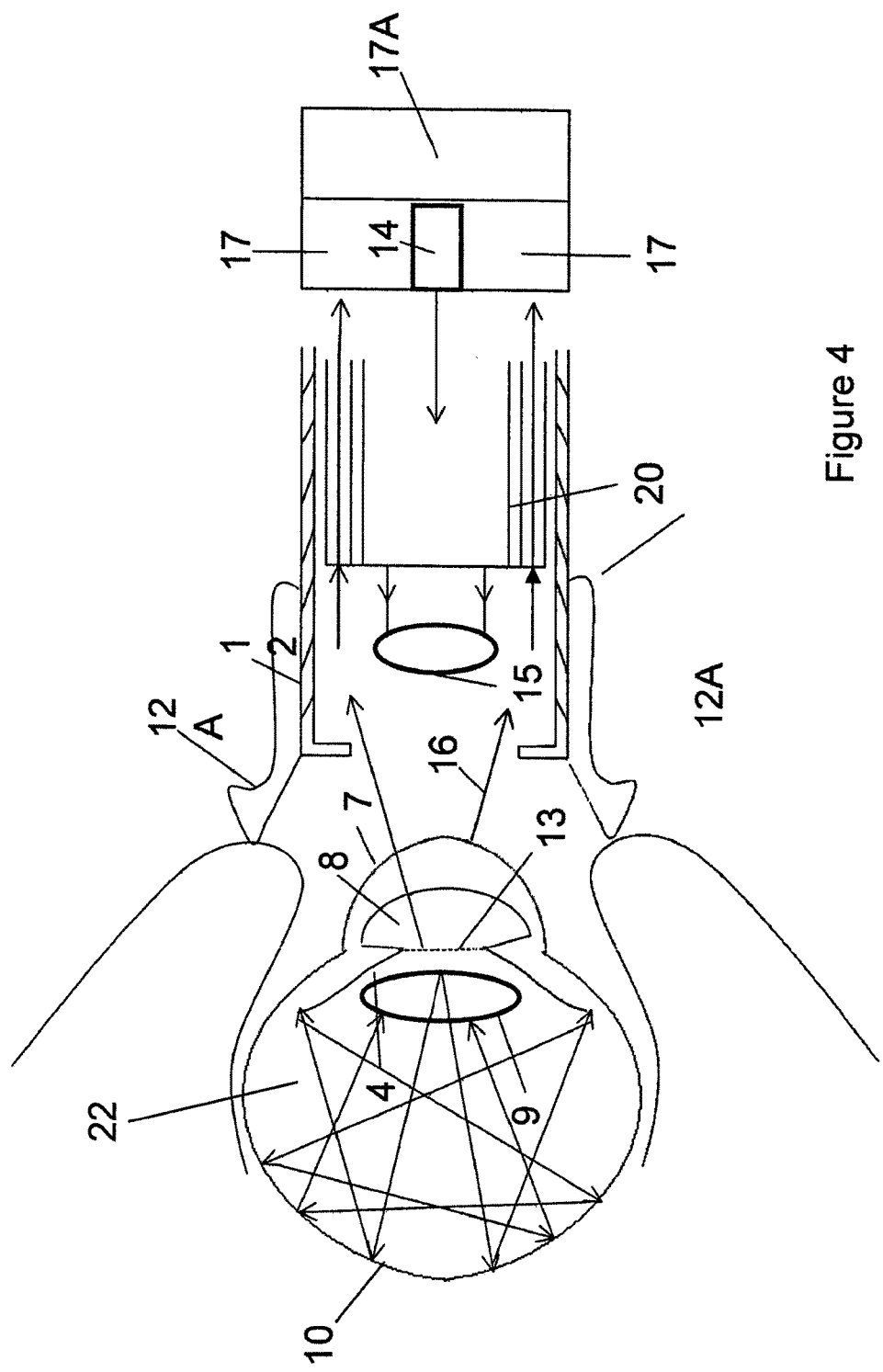
FIG. 4 shows a schematic representation of the first optical system of FIG. 3 during receipt of direct and diffuse light returning from the eye.

In FIG. 4 there is illustrated multiple reflection and scattering of the illumination light within the posterior chamber 22 of the eye prior to the light emerging out of the pupil 13 and arising when the light output from the device is directed in the plane of the pupil 13 according to the illustration of FIG. 3. Of course, for the FIGS. 3 and 4 arrangements the illuminating light can be directed to the retina 10 for direct reflectance there from, or diffuse reflectance if required and as illustrated in FIG. 4.

In the illustrated embodiment, processing means 17A are provided for analysing the light that returns from the eye and as described in further detail below.

Advantageously, the first light source 14 is arranged to provide one or more pulses of illumination light, preferably a stream of pulses, and the receiving/processing means 17 is arranged to record the frequency and/or intensity of light returning from the eye intermittently at a selected timing relative to said pulses so as to effectively discriminate between the light directly and diffusely reflected from different structures such as one or more of the cornea 7, iris 4 and lens 9 of the eye, or to discriminate between diffusely and directly reflected light as returned to the device. In a preferred arrangement, the light recorded is primarily recorded at a time or times when the light source 14 is not emitting light or is switched off. This may be achieved by intermittent actuation of the receiving means or appropriate sampling of the data received, e.g. by means of software. This can mean that the majority of the light recorded is selectively light that is returning by direct or diffuse reflection from the relevant structure, or for example light returning from the retina 10 and that has undergone multiple reflections within the eye and so comprises diffuse light. In this manner, the eye is in effect being used selectively as a cuvette and/or integrating sphere for the monitoring of physiological and physical changes in all structures of the eye.

It should also be noted that the smaller the pupil size, and hence the smaller the exit aperture for the light, the more diffuse the output light will be as more of the light will undergo multiple reflections before exiting through the pupil. The use of selective focussing means to focus light as required on a particular structural feature of the eye, or in the plane of the pupil so the eye can be illuminated through a small pupil rather than dilating the pupil or manipulating the eye, proves advantageous.

As will be appreciated, the invention advantageously provides for a device and method in which the illuminating light can be accurately directed to a particular structure for a part of the human or animal subject's eye and which provides for direct and/or diffuse reflectance which can be analyzed in accordance with the present invention for inspection, measurement and/or monitoring of the physiological and/or physical characteristics, and if required changes thereof, of the subject's eye. For example, direct reflectance from different surfaces within the eye such as the cornea, aqueous humor, lens, iris, vitreous humor and retina can be produced through the accurate control of the timing relationship between the illuminating and reflective light pulses. It is then readily possible to discriminate between direct reflectance returning from such various surface structures for subsequent analysis. Diffuse reflection from these structures would be separated via the second receiving means.

The physiological and/or physical characteristics, and changes thereof, relating to such surface structures can therefore readily be inspected, measured and monitored and a further degree of discrimination can also be achieved through the selective use of the illuminating light of a particular wavelength. As noted above, through the appropriate control of a timing relationship between the illuminating and reflected light pulses to readily discriminate between light returning through the action of the eye as an integrating sphere, i.e. monitoring measuring and inspection of diffuse reflectance, and through the use of the eye as a cuvette when analysis of only the direct reflectance is required.

An integrating sphere is an ideal optical diffuser and is used, for example, in radiometric measurements, where uniform illumination is essential. Light input into an integrating sphere is uniformly reflected and scattered around the sphere's interior so the output is a uniform, spatially integrated beam which is insensitive to spatial, angular or polarisation changes in the input light. In the described invention the light source/intensity is the same each time because the lights focussed in the plane of the pupil. The optical path is also constant for each individual eye. Beam movements can arise due to movement of components of the eye. The refractive index of the Cornea, Aqueous Humor, Lens and Vitreous Humor remain the same for each individual eye as does the air path.

Integrating spheres are usually designed so there is not a direct path from the input to the output thereof. The input and output are thus usually located at different positions and baffles provided to block direct paths there between.

The present invention benefits from the realisation that the eye itself can be used either as a cuvette or integrating sphere so that measurements taken by the device are not subject to variations in the light source. However, as the eye only has a single input/output port, i.e. the pupil, and as light has to pass through reflective interface to enter the eye through the pupil, means have to be found to prevent input light which is reflected directly or diffusely back by these interfaces from swamping the diffuse light which has undergone reflection within the eye or of course vice versa. The present invention achieves this by the use of pulsed illumination and the selected timing of intermittent recording of light returning from the eye relative to the illumination pulses, and also through selective use of light of determined wavelengths so as to benefit from the natural filtering characteristics of the eye and its various component structures.

A further significant advantage of using pulsed illumination light is that this helps reduce problems, e.g. due to heating, which can arise if the retina receives too much illumination from the light source 14. Heating can alter the properties of the blood as well as cellular and metabolic activity and may cause damage to the eye. The use of steady, continuous illumination, whilst enabling measurements to be made in carefully controlled conditions, e.g. in a laboratory, may preclude use in a practical device, particularly if measurements need to be taken frequently, e.g. several times a day.

In addition, by providing illumination pulses over a relatively short-period, e.g. for a few milliseconds, and recording light received during this period, the pulsatable component, i.e. variation in the quantity being sensed due to the pulsing blood flow in the blood vessels of the retina, can be reduced or eliminated. In contrast, the prior art which illustrates the retina continuously has to provide complex systems for recording measurements in time with the pulses in the blood flow to eliminate the pulsatable component.

The length of each pulse of illumination and the wavelength used will differ in dependence upon the substance or reaction to be measured. Typically, each illumination pulse may last between 0.1 milliseconds and a few seconds. The interval between illumination pulses will also depend on the substance or reaction being measured but, typically, would also be in the range 0.1 milliseconds to several seconds.

Although a single pulse could be used, the eye is preferably illuminated by a train of at least six pulses, and preferably more, with a measurement being recorded after each pulse and a mean and standard deviation calculated.

FIGS. 8A, 8B and 8C illustrate the timing of the illumination pulses and the recording periods in three different regimes:
1. Illumination period of 0.1 milliseconds and recording immediately after the pulse then repeat six times at intervals of 10 milliseconds (FIG. 8A).
2. Illumination period of 0.1 milliseconds, record after illumination has been off for 1 millisecond and then repeat this cycle six times with a 10 millisecond gap between each cycle (FIG. 8B).
3. Illuminate for 1 millisecond, start recording 0.1 milliseconds before the end of the illumination period for 1 millisecond and repeat for six cycles with a 10 millisecond gap between each cycle (FIG. 8C).

The following time intervals are shown in FIGS. 8A, 8B and 8C:
P: period between each illumination pulse and each recording interval, e.g. 10 milliseconds.
I: duration of an illumination pulse, e.g. 0.1 or 1.0 milliseconds.
R: duration of a recording period, e.g. 1.0 millisecond.
D: delay between end of illumination pulse and commencement of recording period, e.g. 1.0 millisecond.
O: overlap between illumination pulse and recording period, i.e. time interval between commencement of recording period and end of illumination pulse, e.g. 0.1 milliseconds.

As will be appreciated, the relationship between the pulses is advantageously selected and controlled as required so as to differentiate between different directly and diffusely reflected pulses and also to discriminate between directly reflected and diffusely reflected light pulses as discussed above.

The first optical system may be self-supporting and so can be part of apparatus in front of which the subject is located. The subject positions their eye so as to receive the illumination light. Preferably, a flexible cowl 12A is provided around the housing 12 against which the subject can rest his eye. The cowl 12A may also serve to exclude extraneous light from the eye where the ambient light includes frequencies that are being monitored. Such cowls are well-known on other optical instruments e.g. around the lens of a telescope or pair of binoculars. The cowling also helps locate the subject's eye relative to the device and so defines the distance between the device and the subject's eye.

As described in WO02/071932, a second optical system (not shown) may be used to locate the centre of the pupil 13, and alignment means (not shown) used to align the illumination light from the first optical system so that light is shone through the centre of the pupil 13 in the plane of the pupil 13, that is in a Maxwellian view. The alignment process can be effected, for example, by means of a joystick (not shown), which can be operated by the physician, or the subject themselves. In this way, the operator can view an image of the eye being investigated on a screen (not shown) and use the joystick to align the first optical system with the centre of the pupil 13. Further details of this alignment process are known from WO90/12534 so will not be described further.

However, the device may also be arranged such that the second optical system operates automatically (i.e. with manual operation). Thus, the second optical system may directly activate the alignment means to position the first optical system into the required alignment with the pupil.

Further, instead of the operator viewing the image of the eye on a screen, the image may be transferred directly onto the retina or required structure of the operator, for example by way of the first optical system itself.

As shown in FIGS. 1 to 4 input light 14 is directed via an optical fibre 20 from which it is emitted so as to pass through focussing means 15 towards the desired site within the structure of the eye whether at the front or back of the eye as noted herein. In FIG. 1 the light is focussed on the lens for direct or diffuse reflectance there from, and in FIG. 3 the light is focussed at the centre of the pupil 13 for direct and diffuse reflectance from the retina 10 and so as to be reflected back as illustrated in FIG. 4. Light 16, which returns from the eye back through the pupil 13, subsequently passes back into the device and travels as a beam 17 along one or more optical fibres 21 to the receiving means 17.

Independent of the nature of the reflectance being inspected measured or monitored, the processing means 17A analyses the beam, e.g. to determine the absorbance/reflectance spectrum of the retina and/or the retinal blood vessels. Any combination of mono-chromatic light or white light, as well as wavelengths in the infra-red, near infra-red or ultra-violet spectra can be used. For example, specific selected wavelengths permit optimal discrimination of, for example physical and physiological characteristics of the eye and any changes thereof in addition, if required, to the various blood components, as well as optimal discrimination of the various retinal biochemical functions and components.

In this way, it is, for example, possible to provide monitoring and inspection of physiological and physical characteristics of the eye.

Figure 5:
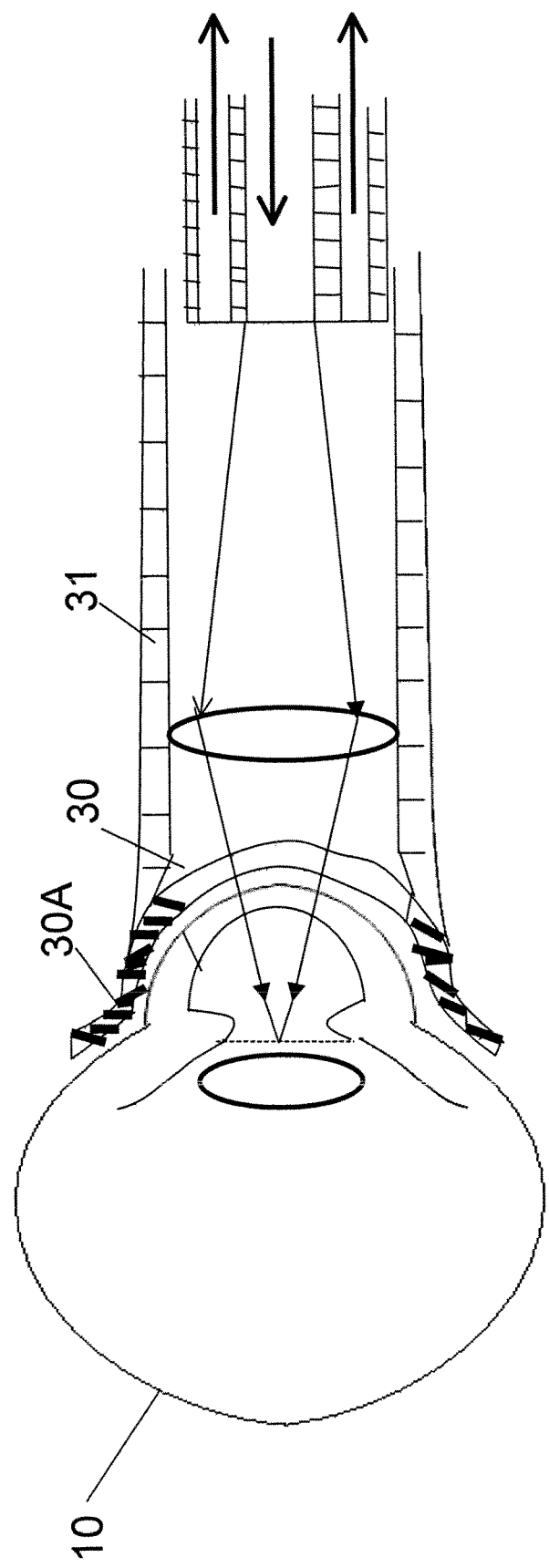
FIGS. 5 and 6 are schematic representations of the first optical system of a second embodiment of the eye during illumination of the eye and receipt of light returning there from, respectively.
Figure 6:
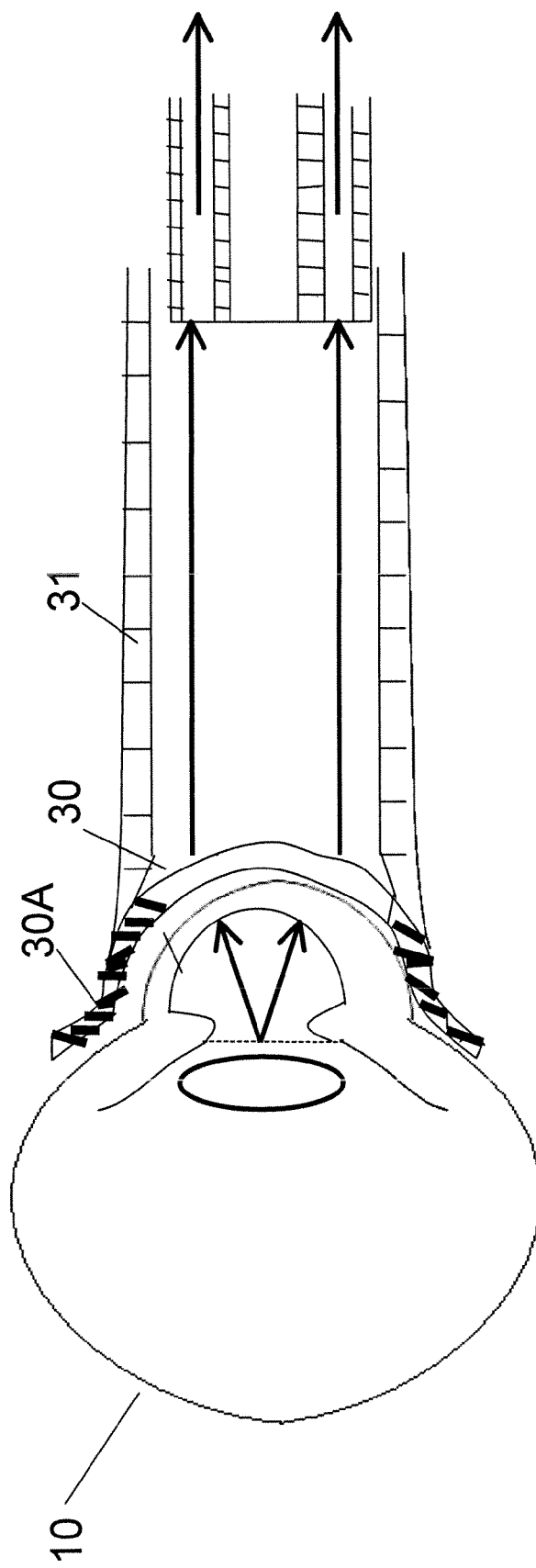

FIGS. 5 and 6 correspond to FIG. 1-4 but show a device in which part of the optical system is mounted on a scleral contact lens 30. The use of such a lens 30 to support the device is described further in WO90/12534. Portions 30A of the contact lens extending beyond housing 31 may be coloured black if it is desirable to exclude extraneous light from entering the device. The operation of the device shown in FIGS. 5 and 6 is otherwise similar to that shown in FIGS. 1 to 4.

Figure 7:
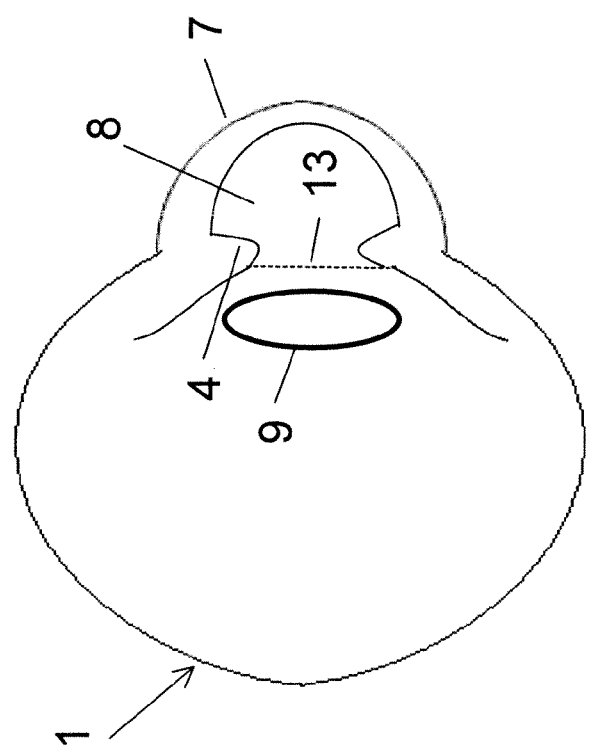
FIG. 7 is a schematic representation of a third embodiment pupillometery of the invention.

In a further arrangement, shown schematically in FIG. 7, the illumination means 40 and receiving means 41 may be located remotely from the eye but positioned to direct illumination into the eye and receiving light returning there from. Processing means 41A is also shown. In this embodiment, the illumination light need not be focussed in the plane of the pupil but simply directed into the eye.

The system described above can be used for a wide range of applications relating to physiological and physical characteristics of the human or animal eye.

In particular for iris recognition and measurement of blood alcohol for example for people controlling heavy machinery or driving cars.

Also, the illumination and recording of light may be used in a variety of analysis methods, e.g. to monitor the absorbance of specific wavelengths, to carry out diffuse reflectance spectroscopy, to carry out Raman spectroscopy (in which the illuminating light stimulates light emission from the eye which is then detected) or fluoroscopy or use of frequencies in the terahertz range.

Further, it is possible also to use the system to measure the unique DNA profile of any individual and thus provide security checks. For example, a monocular system can be used as part of a cash-dispensing machine, in which the identity of the person wishing to withdraw cash is checked via non-invasive DNA analysis of the retinal cells or other cells in any of the structures of the eye. Alternatively, or additionally, the second optical system may be used to identify the subject by iris identification.

Identification of the subject in this may be used for security and/or legal reasons. It may also be used by the processing means 17A to associate the subject's identity with the measurements being taken for recording purposes.

As known, it is also possible to measure changes in the arteries and veins of the retina, which may be an indication of generalised arterial and venous disease. Thus in diabetic patents, who typically can suffer from such generalised arterial disease, it would be possible to non-invasively chart the progression of the disease.

The system can measure visual evoked potentials more accurately than conventional means, because it is possible to give an accurate amount of light and so the amplitude of response can also be assessed. Conventionally, by contrast, only latency of response is measured. Thus, the present system allows for the assessment of any electrical activity of the retina, so that the activity of the visual areas of the brain can be assessed.

Also, the measurements made possible with the present system can be of static samples or of continuous samples in real time.

As will be appreciated, the present invention advantageously employs the anatomical and physiological characteristics of the eye to enhance the efficiency and accuracy with which the eye can be employed as a component of a spectrophotometer.

The invention further allows for the advantageous differentiation between reflectance of illuminating light from the cornea, iris, lens, aqueous humor, vitreous humor and also the retina and so it becomes readily imposable to investigate changes in reflectance from any or all of these structures.

Of course, the invention is not restricted to the details of a specific embodiment noted above and any appropriate number of light sources and receivers, for example two of each can be employed as required. Further, the focussing system employed within the device of the present invention can advantageously be moved forwards and backwards all quadrants to focus the light as appropriate on any particular structure and, if required, in the plane of the pupil.

Any data received from the reflected light can be analysed within the device or transmitted remotely therefrom by any appropriate wire or wireless, transmission means. Of course, the light employed within the present invention can be polarized as required and provided at any appropriate wavelength.

The invention claimed is:

1. A device for use in non-invasive inspection, measurement and/or monitoring of a human or animal subject's eye, the device comprising:
   a first optical system which comprises:
   a housing;
   a cowl coupled with the housing and configured to exclude from the eye all extraneous light;
   a focusing lens that is adjustable to focus light in a controllable and selective manner to any required structural feature of the eye;
   an illumination means for selectively directing illumination light onto the eye through the focusing lens to produce direct and diffuse reflectance returning from a posterior chamber of the eye and to produce direct and diffuse reflectance returning from a selected structure and for providing the illumination light in one or more pulses, wherein the selected structure is selected from the any required structural feature of the eye, and wherein the focusing lens, the illumination means, and the eye are substantially aligned with one another; and
   a first receiving means for receiving directly reflected light returning from the eye as a result of illumination by the illumination light; and
   a second receiving means positioned on the cowl and configured to receive diffusely reflected light returning from the eye as a result of illumination by the illumination light, wherein the first receiving means and the second receiving means are arranged to:
      distinguish between (1) the directly and diffusely reflected light returning from the posterior chamber serving as an integrating sphere and (2) the directly and diffusely reflected light returning from the selected structure by discriminating the illumination light with a threshold wavelength, wherein the threshold wavelength is 1400 nm; and
      record the returning directly and diffusely reflected light intermittently based on a selected timing relationship between the one or more pulses of illumination light and the direct and diffuse reflectance so as to discriminate between (1) the directly and (2) diffusely reflected light returning from the posterior chamber for analysis of the directly and diffusely reflected light.

2. A device as claimed in claim 1 in which the receiving means are arranged to record during a recording period after each pulse of illumination light, the recording period commencing at the end of the pulse of illumination light or at a predetermined time interval before or after the end of the pulse of illumination light.

3. A device as claimed in claim 1 in which the illumination means is arranged to, along with the focusing lens, focus the illumination light on the first structure of the eye.

4. A device as claimed in claim 1 in which the receiving means are arranged to monitor the intensity of light of a selected wavelength returning from the first structure of the eye.

5. A device as claimed in claim 1 in which the receiving means are arranged to monitor the intensity of light of different wavelengths returning from the first structure thereby enabling an absorbance/reflectance characteristic of the first structure to be determined.

6. A device as claimed in claim 1 comprising a second optical system arranged to determine the location of the second structure of the eye.

7. A device as claimed in claim 6 in which the second optical system is arranged to identify the subject by iris identification or DNA.

8. A method of non-invasive inspection measurement and/or monitoring of a human or animal subject's eye, comprising:
   positioning the subject relative to a cowl of a housing of an optical system, wherein the cowl is configured to exclude extraneous light from the eye;
   selecting a structure of the eye to monitor;
   adjusting a focusing lens based on the selected structure to focus light on the selected structure, wherein the focusing lens is configured to focus light in a controllable and selective manner to any required structural feature, and wherein the selected structure is selected from the any required structural feature;
   selectively directing one or more pulses of illumination light onto the eye through the focusing lens to produce direct and diffuse reflectance returning from a posterior chamber of the eye and to produce direct and diffuse reflectance returning from the selected structure, wherein a timing relationship between the one or more pulses of illumination light and the direct and diffuse reflectance is selected based on the selected structure, and wherein the focusing lens, a source of the one or more pulses of illumination light, and the eye are substantially aligned with one another;
   receiving directly reflected light returning from the eye as a result of illumination by the illumination light using a first receiving means; and
   receiving diffusely reflected light returning from the eye as a result of illumination by the illumination light using a second receiving means positioned on the cowl;
   distinguishing between (1) directly and diffusely reflected light returning from the posterior chamber serving as an integrating sphere and (2) the directly and diffusely reflected light returning from the selected structure by discriminating the illumination light with a threshold wavelength, wherein the threshold wavelength is 1400 nm; and
   recording the directly and diffusely reflected light returning from the eye as a result of such illumination, wherein the directly and diffusely reflected light are recorded intermittently based on the timing relationship relative to the one or more pulses so as to discriminate between (1) the directly and (2) diffusely reflected light returning from the posterior chamber and other reflected light for analysis of the directly and diffusely reflected light.

9. A method of non-invasive inspection, measurement and/or monitoring of a human or animal subject's eye, comprising:
   positioning the subject relative to a cowl of a housing of an optical system, wherein the cowl is configured to exclude extraneous light from the eye;
   selecting a structure of the eye to monitor;
   adjusting a focusing lens based on the selected structure to focus light on the selected structure, wherein the focusing lens is configured to focus light in a controllable and selective manner to any required structural feature, and wherein the selected structure is selected from the any required structural feature;
   selectively directing one or more pulses of illumination light onto the eye through the focusing lens to produce direct and diffuse reflectance returning from an anterior chamber of the eye and to produce direct and diffuse reflectance returning from the selected structure, wherein a timing relationship between the one or more pulses of illumination light and the direct and diffuse reflectance is selected based on the selected structure, and wherein the focusing lens, a source of the one or more pulses of illumination light, and the eye are substantially aligned with one another;
   receiving directly reflected light returning from the eye as a result of illumination by the illumination light using a first receiving means; and
   receiving diffusely reflected light returning from the eye as a result of illumination by the illumination light using a second receiving means positioned on the cowl;
   distinguishing between (1) directly and diffusely reflected light returning from the anterior chamber of the eye and (2) the directly and diffusely reflected light returning from the selected structure; and
   recording the directly and diffusely reflected light returning from the anterior chamber of the eye as a result of such an illumination, wherein the directly and diffusely reflected light are recorded intermittently based on the timing relationship relative to the one or more pulses so as to discriminate between (1) the directly and (2) diffusely reflected light returning from the anterior chamber and other reflective light for analysis of the directly and the diffusely reflected returning light.

10. A device as claimed in claim 1 in which the first receiving means and the second receiving means are configured to:
   receive reflected light with wavelengths above 1400 nm;
   determine that the reflected light with wavelengths above 1400 nm have arisen through direct or diffuse reflectance from a structure other than the posterior chamber; and
   ignore the reflected light with wavelengths above 1400 nm based on the determination.

11. A device as claimed in claim 1 in which the second receiving means is disposed on the cowl at an angle of about 45°.

12. A method as claims in claim 8, further comprising:
   receiving reflected light with wavelengths above 1400 nm;
   determining that the reflected light with wavelengths above 1400 nm have arisen through direct or diffuse reflectance from a structure other than the posterior chamber; and
   ignoring the reflected light with wavelengths above 1400 nm based on the determination.

13. A method as claimed in claim 8 in which the second receiving means is disposed on the cowl at an angle of about 45°.

14. A method as claims in claim 9, further comprising:
receiving reflected light with wavelengths above 1400 nm;
determining that the reflected light with wavelengths above 1400 nm have arisen through direct or diffuse reflectance from a structure other than the posterior chamber; and
ignoring the reflected light with wavelengths above 1400 nm based on the determination.

15. A method as claimed in claim 9 in which the second receiving means is disposed on the cowl at an angle of about 45°.

* * * * *